United States Patent [19]

Fukuma

[11] Patent Number: 5,116,122
[45] Date of Patent: May 26, 1992

[54] SPECTROPHOTOMETER

[75] Inventor: Toshiaki Fukuma, Kyoto, Japan

[73] Assignee: Shimadzu Corporation, Kyoto, Japan

[21] Appl. No.: 669,467

[22] Filed: Mar. 14, 1991

[51] Int. Cl.$^5$ ............................................. G01J 3/42
[52] U.S. Cl. ................................... 356/326; 364/498
[58] Field of Search ............. 356/319, 326, 328, 244, 356/418, 419; 364/498, 526

[56] References Cited

U.S. PATENT DOCUMENTS

| | | | |
|---|---|---|---|
| 3,704,953 | 12/1972 | Carter et al. | 356/326 |
| 4,482,251 | 11/1984 | Saylor | 356/418 |
| 4,645,343 | 2/1987 | Stockdale et al. | 356/326 |
| 4,935,875 | 6/1990 | Shah et al. | 356/319 |

FOREIGN PATENT DOCUMENTS

| | | | |
|---|---|---|---|
| 0303707 | 2/1989 | European Pat. Off. | |
| 100644 | 5/1987 | Japan | 356/326 |
| 167273 | 7/1988 | Japan | 356/326 |
| 8706008 | 10/1987 | PCT Int'l Appl. | |

OTHER PUBLICATIONS

Patent Abstracts of Japan vol. 11, no. 308, (P-624)(2755) Oct. 8, 1987 & JP-A-62 100 644 (Shimadzu) May 11, 1987 "abstract".
International Laboratory, vol. 15, no. 3, Apr. 1985, Fairfield, CT, USA pp. 40-47; M. D. Boland et al.: "A step-programmable computing UV/VIS spectrophotometer".
Review of Scientific Instruments, vol. 59, no. 6, Jun. 1988, New York, USA, pp. 940-950; J. S. Lindsey et al.: "Robotic work station for microscale synthetic chemistry: on-line absorption spectroscopy, quantative . . . ". International Laboratory, vol. 18, no. 5, Jun. 1988, Fairfield, CT, USA, pp. 33-43; C. S. C. Tarbet: "Design of an advance performance UV scanning spectrophotometer".

Primary Examiner—F. L. Evans
Attorney, Agent, or Firm—Wegner, Cantor, Mueller & Player

[57] ABSTRACT

A spectrophotometer provided with: a sample changer for holding a plurality of samples to be analyzed, each of which is given an identification code, and positioning a selected one of the samples for measurement; means for setting a measuring wavelength for each of the identification codes of the samples; means for setting an identification code for the measured data of each of the samples; means for setting a coefficient to be used for processing the measured data of each of the samples together with an identification code; means for setting an operation expression composed of the identification codes of the measured data of the samples and the identification code of the coefficient; means for storing the data obtained by measuring each of the samples with the corresponding one of the wavelengths set for the sample held by the sample changer in correspondence with the corresponding one of the identification codes of the measured data; and means for reading out the data stored in the storing means and the coefficient set in the setting means in accordance with the identification codes of the measured data and the coefficient which constitute the operation expression set in the setting means, and performing an operation for data processing in accordance with the operation expression.

3 Claims, 2 Drawing Sheets

Fig. 2

| CELL | λ | k | A·k |
|------|-------|-------|-----|
| C1 | 500.0 | 1.000 | A1 |
| C2 | 500.0 | 0.5 | A2 |
| C3 | 600.0 | 0.7 | A3 |
| C4 | B | B | B |
| ' | ' | ' | ' |
| ' | ' | ' | ' |

SPECTROPHOTOMETER

This invention relates to a spectrophotometer provided with an automatic sample changer and means for processing the data obtained by measurement of a sample.

Some spectrophotometers are provided with an automatic sample changer as an attachment. In spectrometric analysis, when many samples of the same kind are to be measured, only the samples are changed while the measuring wavelength and the manner of processing the measured data are kept unchanged. When samples of different kinds are to be analyzed, however, generally the measuring wavelength and the manner of processing the measured data are changed with each of the samples.

In known spectrophotometers, for processing the measured data choice can be made only among several preset data processing patterns, and it is impossible to preset a different measuring wavelength for each of the samples to be analyzed. As a result, in very few cases the automatic sample changing function can be fully utilized to improve the efficiency of analysis, and many manual operations are required for analysis of samples of different kinds, and an additional computer must be provided to attain a higher degree of automatic operation of the instrument. This poses of economic problem.

SUMMARY OF THE INVENTION

Accordingly, the primary object of the invention is to improve the efficiency of operation of a spectrophotometer in measuring samples of different kinds and processing the measured data.

The object of the invention is attained by a spectrophotometer which comprises:

a light source;

a monochromator for dispersing the light from the light source into a sequence of wavelengths to provide a monochromatic light of a selected one of the wavelengths;

a sample changer for holding a plurality of samples to be analyzed, each of which is given an identification code;

means for setting a measuring wavelength for each of the identification codes of the samples;

means for driving the sample changer to position a selected one of the samples in the path of the monochromatic light from the monochromator;

means for driving the monochromator to provide a monochromatic light of that one of the wavelengths preset in the setting means which corresponds to the identification code of the selected one of the samples;

means for setting an identification code for the measured data of each of the samples;

means for setting a coefficient to be used for processing the measured data of each of the samples together with an identification code;

means for setting an operation expression composed of the identification codes of the measured data of the samples and the identification code of the coefficient;

means for storing the data obtained by measuring each of the samples held by the sample changer with the corresponding wavelength set for the sample in correspondence with the identification code of the measured data; and means for reading out the data stored in the storing means and the coefficient set in the setting means in accordance with the identification codes of the measured data and the coefficient which constitute the operation expression set in the setting means, and performing an operation for data processing in accordance with the operation expression.

Since each of the samples held by the sample changer is given an identification code, in correspondence to which a measuring wavelength is set, it is possible to drive the monochromator to a predetermined wavelength position for each of the samples in ganged relation to changing samples.

Since the measured data of each of the samples obtained in this manner is given an identification code beforehand and stored together with the identification code in a memory, the data can be taken out by their respective identification codes if and when required for data processing to be performed later.

Since each of the coefficients necessary for data processing is also given an identification code. It is possible to read out the coefficients by their respective identification codes.

Since the operation expressions for data processing are composed of the above-mentioned identification codes, it is possible to perform data processing by a required operation expression by taking out necessary data by the corresponding identification codes. Therefore, the contents of data processing are not fixed but can be set freely by the operator, so that it is possible to conduct an operation for processing the measured data of each sample.

The invention will be described in detail with reference to the accompanying drawings.

BRIEF DESCRIPTION OF THE DRAWINGS

FIG. 2 shows a picture presented on the display of the instrument of the invention at a step of entering data required for analysis into the central processing unit of the instrument; and FIG. 3 shows another picture presented on the display at a second step of entering data required for processing into the central processing unit of the instrument.

DESCRIPTION OF THE PREFERRED EMBODIMENT

Figure 1:
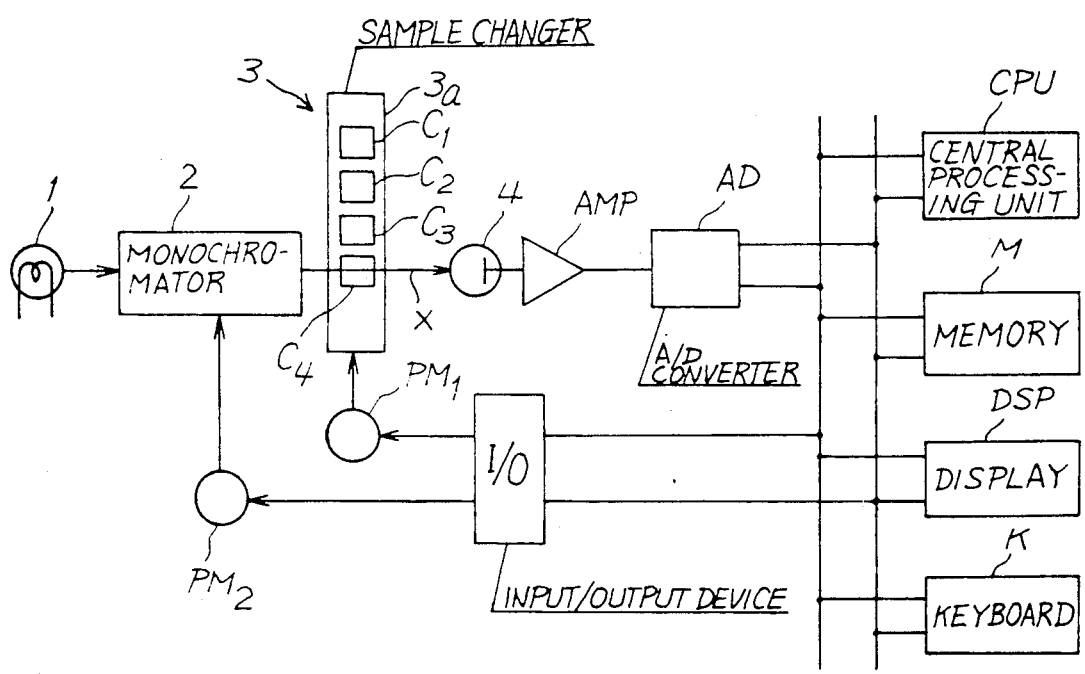
FIG. 1 is a schematic layout of a spectrophotometer constructed in accordance with the invention.

Referring to FIG. 1, there is schematically shown a spectrophotometer constructed in accordance with the invention comprising a light source 1, a monochromator 2, a sample changer 3, a photodetector 4, an amplifier AMP, an analog-to-digital converter AD and a central processing unit CPU. The sample changer 3 comprises a frame 3a for holding a plurality, say, four samples $C_1 \sim C_4$, a pulse motor $PM_1$ and a mechanism driven by the motor to selectively position one of the samples in the optical path X of the monochromatic light from the monochromator 2. A central processing unit CPU produces a control signal to be applied through an input/output device I/O to the pulse motor $PM_1$. The monochromator 2 includes a dispersing element which disperses the light from the source 1 into a sequence of wavelengths. A pulse motor $PM_2$ drives the dispersing element so that monochromatic light of a selected one of the wavelengths is passed through one of the samples positioned in the optical path X into the photodetector 4, which converts the light to a corresponding electrical signal.

The output signal from the photodetector 4 is amplified by the amplifier AMP and converted into a corresponding digital signal by the A/D converter AD and then stored in a memory M.

The central processing unit CPU provides a control signal to be applied through the input/output device I/O to the pulse motor $PM_2$ to drive the motor for wavelength scanning. A keyboard K is provided to input necessary data into the central processing unit CPU. A display DSP such as a cathode ray tube is provided for displaying various instructions or commands for operation of the instrument as well as the results of measurement.

FIGS. 2 and 3 respectively show a picture presented on the tube face of the display DSP when control commands for the operation of analysis are entered into the central processing CPU. When the central processing unit CPU is initially set to an automatic analysis mode, a table as shown in FIG. 2 appears on the tube face of the display DSP. The table has four columns CELL, $\lambda$, k and A·k, each having as many locations as there are samples to be analyzed. In each of the locations of the column CELL an identification code $C_1, C_2, C_3, \ldots C_n$ is given corresponding to each of the samples $C_1 \sim C_n$ set in the sample changer 3. The operator enters necessary data into the columns $\lambda$ and k. In each of the locations of the column $\lambda$ a wavelength on the order of nanometers at which one of the samples is to be measured is entered such as, for example, 500 nm, 600 nm, etc. In each of the locations of the column k a coefficient to be multiplied with the value of the corresponding one of the samples measured at the corresponding one of the wavelengths given in the column $\lambda$ is entered. In each of the locations of the column A·k a code $A_1, A_2, A_3, \ldots$ is entered which designates the result of multiplication of each of the measured values with the corresponding one of the coefficients entered in the column k. In the illustrated table, a code B is entered in the fourth location from above in each of the four columns. The code B indicates that the cell $C_4$ contains only a blank sample, that is, solvent. When a sample is designated as "blank", the measured value of the "blank" sample is automatically subtracted from the measured value of each of the other samples.

When entry of data in the table shown in FIG. 2 has been completed, the picture on the tube face of the display DSP changes to the picture shown in FIG. 3, which present a message that an operation expression be set. Operation symbols are given in the uppermost row of the picture, with a triangular mark below indicating a cursor. The operator moves the cursor in accordance with the required operation expression to successively bring the cursor below the required one after another of the operation symbols and successively presses an input key on the keyboard, whereupon the selected symbols are successively entered into the central processing unit CPU to form the required expression.

A blank area is provided below the cursor and the operation expression that has been set appears in a frame in the lowermost portion of the tube face. In the blank area the coefficients necessary for the operation are presented in numerical values with their respective identification codes. To put it in detail, the operator writes in the blank area identification codes $K_1, K_2$, etc. and corresponding concrete numerical values, for example, 2.654, etc., and then in the frame an operation expression for data processing such as $$K_1(A_1-A_2)/A_3,$$

whereupon the expression is entered into the central processing unit CPU. Here, $K_1$ is given in the picture of FIG. 3, and $A_1, A_2$ and $A_3$ are given in the picture of FIG. 2. The above expression indicates that a calculation is to be performed with those values which are obtained by multiplication of the measured values of the samples $C_1, C_2$ and $C_3$ by the corresponding coefficients k having been substituted for the terms $A_1, A_2$ and $A_3$, respectively, of the expression.

Suppose that the measured values of the samples $C_1, C_2, C_3$ and $C_4$ at their respective designated wavelengths are $a_1, a_2, a_3$ and $a_4$, respectively. The expression will be $$2.654\{(a_1-a_4)-0.5(a_2-a_4)\} \div 0.7(a_3-a_4'),$$

wherein $a_4$ and $a_4'$ are the measured values of the sample $C_4$ at 500 nm and 600 nm, respectively.

The above description may give an impression that only one operation can be performed for processing the measured data obtained from the four kinds of samples. An operation expression can be set for each of the samples $C_1$ to $C_n$ as a function of $A_1$ to $A_n$, such as $$F_1(K_1A_1)$$
$$F_2(K_2A_2)$$
$$\vdots$$
$$F_n(K_nA_n)$$

It is also possible to set two or more wavelengths for one sample by putting the same identification code $C_n$ in two or more locations of the column CELL and different wavelengths $\lambda_1, \lambda_2$, in the corresponding locations of the column $\lambda$ in the table shown in FIG. 2, such as

| CELL | $\lambda$ | |
|---|---|---|
| . | . | . |
| . | . | . |
| $C_n$ | $\lambda_1$ | . |
| · $C_n$ | $\lambda_2$ | . |
| $C_{n-1}$ | . | . |
| . | . | . |

After the measuring wavelength, the required coefficient and the operation expression for data processing for each of the samples to be analyzed have been set in the above-mentioned manner, an instruction is given to the central processing unit CPU to initiate analysis, whereupon in accordance with the table shown in FIG. 2 the central processing unit drives the sample changer to select one of the samples $C_1, C_2, \ldots C_n$ held therein selects the wavelength of the monochromator set for the selected sample, takes in the measured value, multiplies the measured value by the coefficient $k_1, k_2, \ldots$ or $k_n$ set for the measured sample, and causes the value obtained as a result of the multiplication and the corresponding identification code $A_1, A_2, \ldots$ or $A_n$ to be stored in the memory M. After the measurement has been finished, the central processing unit CPU reads out the data stored in the memory, processes the data in accordance with the set operation expression, and then causes the output device such as a printer to print out the result of the operation.

In known spectrophotometers provided with an automatic sample changer it is impossible to set a different wavelength for each sample to be analyzed, and for processing the measured data choice can be made only among those operation expressions which are stored beforehand in a controller, with resulting lack of flexibility in measurement of different kinds of samples.

In accordance with the invention it is possible to set a measuring wavelength for each sample to be analyzed, and the operation expression for processing the data obtained from measurement of a sample is not fixed but can be formed freely by the operator, so that it is possible to efficiently use the function to automatically change samples, and freely analyze different kinds of samples, with resulting increase in flexibility of operation of the spectrophotometer.

What I claim is:

1. A spectrophotometer comprising:
   a light source;
   a monochromator for dispersing the light from said light source into a sequence of wavelengths to provide a monochromatic light of a selected one of said wavelengths;
   a sample changer for holding a plurality of samples to be analyzed, each of which is given an identification code $C_1, C_2, \ldots C_n$;
   means for setting a measuring wavelength $\lambda_1, \lambda_2, \ldots \lambda_n$ for each of said identification codes of said samples;
   means for driving said sample changer to position a selected one of said samples in the path of said monochromatic light from said monochromator;
   means for driving said monochromator to provide a monochromatic light of that one of said wavelengths preset in said setting means which corresponds to said identification code of said selected one of said samples;
   means for setting an identification code $A_1, A_2, \ldots A_n$ for the measured data of each of said samples;
   means for setting a coefficient to be used for processing the measured data of each of said samples together with an identification code $K_1, K_2, \ldots K_n$;
   means for setting an operation expression composed of said identification codes $A_1, A_2, \ldots A_n$ of said measured data of said samples and said identification code $K_1, K_2, \ldots K_n$ of said coefficient;
   means for storing the data obtained by measuring each of said samples held by said sample changer with the corresponding wavelength set for said sample in correspondence with the identification code of said measured data; and
   means for reading out said data stored in said storing means and said coefficient set in said setting means in accordance with said identification codes of said measured data and said coefficient which constitute said operation expression set in said setting means, and performing an operation for data processing in accordance with said operation expression.

2. The spectrophotometer of claim 1, wherein said means for driving said sample changer comprises a pulse motor.

3. The spectrometer of claim 1, wherein said means for driving said monochromator comprises a pulse motor.